(12) United States Patent
Bareja et al.

(10) Patent No.: US 9,144,538 B2
(45) Date of Patent: *Sep. 29, 2015

(54) COSMETIC COMPOSITIONS CONTAINING SUBSTITUTED AZOLE AND METHODS FOR ALLEVIATING THE SIGNS OF PHOTOAGED SKIN

(71) Applicant: The Procter & Gamble Company, Cincinnati, OH (US)

(72) Inventors: Supriya Punyani Bareja, New Delhi (IN); Stevan David Jones, Singapore (SG); John Erich Oblong, Loveland, OH (US); Kevin John Mills, Goshen, OH (US); John Crist Bierman, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/167,181

(22) Filed: Jan. 29, 2014

(65) Prior Publication Data

US 2014/0227207 A1 Aug. 14, 2014

Related U.S. Application Data

(60) Provisional application No. 61/762,551, filed on Feb. 8, 2013.

(51) Int. Cl.
| | |
|---|---|
| *A61K 8/49* | (2006.01) |
| *A61K 45/06* | (2006.01) |
| *A61Q 17/04* | (2006.01) |
| *A61Q 19/08* | (2006.01) |
| *A61K 31/4164* | (2006.01) |

(52) U.S. Cl.
CPC ............ *A61K 8/4946* (2013.01); *A61K 31/4164* (2013.01); *A61K 45/06* (2013.01); *A61Q 17/04* (2013.01); *A61Q 19/08* (2013.01)

(58) Field of Classification Search
CPC combination set(s) only.
See application file for complete search history.

(56) References Cited

U.S. PATENT DOCUMENTS

| | | |
|---|---|---|
| 677,302 A | 6/1901 | Wyman et al. |
| 3,146,684 A | 9/1964 | Vanderhoof |
| 3,245,915 A | 4/1966 | Rai et al. |
| 3,755,560 A | 8/1973 | Dickert et al. |
| 3,764,559 A | 10/1973 | Mizuno et al. |
| 4,199,483 A | 4/1980 | Jones |
| 4,421,769 A | 12/1983 | Dixon et al. |
| 4,539,133 A | 9/1985 | Boskamp |
| 4,971,724 A | 11/1990 | Kalota et al. |
| 4,992,195 A | 2/1991 | Dolan et al. |
| 4,992,212 A | 2/1991 | Corring et al. |
| 5,030,377 A | 7/1991 | Sone et al. |
| 5,171,477 A | 12/1992 | Kreh |
| 5,277,836 A | 1/1994 | Peters |
| 5,344,590 A | 9/1994 | Carter et al. |
| 5,534,180 A | 7/1996 | Miracle et al. |
| 5,545,348 A | 8/1996 | Savio |
| 5,547,612 A | 8/1996 | Austin et al. |
| 5,616,546 A | 4/1997 | Miracle et al. |
| 5,647,995 A | 7/1997 | Kneller et al. |
| 5,650,097 A | 7/1997 | Wysong et al. |
| 5,703,030 A | 12/1997 | Perkins et al. |
| 5,772,786 A | 6/1998 | De Smet et al. |
| 5,801,137 A | 9/1998 | Addison et al. |
| 5,804,542 A | 9/1998 | Scheper et al. |
| 5,807,900 A | 9/1998 | Bryce et al. |
| 5,824,630 A | 10/1998 | Christie et al. |
| 5,834,409 A | 11/1998 | Ramachandran et al. |
| 5,843,877 A | 12/1998 | Park et al. |
| 5,858,959 A | 1/1999 | Surutzidis et al. |
| 5,868,820 A | 2/1999 | Claffey |
| 5,904,161 A | 5/1999 | Rai et al. |
| 5,912,218 A | 6/1999 | Chatterjee et al. |
| 5,914,307 A | 6/1999 | DeNome et al. |
| 5,939,082 A * | 8/1999 | Oblong et al. ............... 424/401 |
| 5,951,747 A | 9/1999 | Lewis et al. |
| 6,004,628 A | 12/1999 | Spellane et al. |
| 6,059,867 A | 5/2000 | Lewis et al. |
| 6,130,254 A | 10/2000 | Fisher et al. |
| 6,156,715 A | 12/2000 | Lentsch et al. |
| 6,281,170 B1 | 8/2001 | Marsella et al. |
| 6,365,630 B1 | 4/2002 | Fisher et al. |
| 6,410,495 B1 | 6/2002 | Lentsch et al. |
| 6,649,085 B2 | 11/2003 | Reinhardt et al. |
| 6,656,928 B1 | 12/2003 | McCadden |

(Continued)

FOREIGN PATENT DOCUMENTS

| | | |
|---|---|---|
| DE | 4244031 | 6/1994 |
| EP | 0699745 | 8/1994 |

(Continued)

OTHER PUBLICATIONS

Reichrath, J. "Antimycotics: why are they effective in the treatment of seborrheic dermatitis?" *Dermatology*, 208:174-175, 2004.

(Continued)

*Primary Examiner* — Bethany Barham
*Assistant Examiner* — Barbara Frazier
(74) *Attorney, Agent, or Firm* — John G. Powell

(57) ABSTRACT

Cosmetic compositions for alleviating the signs of photoaged skin containing a substituted azole. Methods for alleviating the signs of photoaged skin that include applying a cosmetic composition comprising substituted azole to a target UV-exposed skin surface. The substituted azole compound present in the cosmetic composition may be 1-phenylimidazole, 4-phenylimidazole or a combination thereof. An effective amount of the cosmetic composition is applied to the target skin surface for a period of time sufficient to alleviate at least one sign of photoaging.

11 Claims, No Drawings

(56) References Cited

U.S. PATENT DOCUMENTS

| | | | |
|---|---|---|---|
| 6,875,734 | B2 | 4/2005 | Reinhardt et al. |
| 6,942,870 | B2 | 9/2005 | Fisher et al. |
| 7,186,416 | B2 | 3/2007 | Popp et al. |
| 8,048,918 | B2 | 11/2011 | Ward et al. |
| 8,633,191 | B2 | 1/2014 | Perry |
| 2003/0229141 | A1 | 12/2003 | Yu et al. |
| 2004/0077721 | A1 | 4/2004 | Yuan et al. |
| 2004/0175347 | A1 | 9/2004 | Bissett |
| 2005/0238672 | A1 | 10/2005 | Nimni |
| 2005/0255048 | A1 | 11/2005 | Hirsh et al. |
| 2006/0246098 | A1 | 11/2006 | Rao et al. |
| 2006/0269485 | A1 | 11/2006 | Friedman et al. |
| 2006/0275237 | A1 | 12/2006 | Bissett et al. |
| 2007/0036731 | A1 | 2/2007 | Hirsh et al. |
| 2007/0082068 | A1 | 4/2007 | Satsu et al. |
| 2008/0014252 | A1 | 1/2008 | DelPrete |
| 2008/0260864 | A1 | 10/2008 | Dascalu |
| 2009/0298897 | A1 | 12/2009 | Cools et al. |
| 2010/0074857 | A1 | 3/2010 | Lipkin et al. |
| 2010/0278784 | A1 | 11/2010 | Pojasek et al. |
| 2014/0227206 | A1 | 8/2014 | Bareja et al. |
| 2014/0227207 | A1 | 8/2014 | Bareja et al. |
| 2014/0227208 | A1 | 8/2014 | Bareja et al. |

FOREIGN PATENT DOCUMENTS

| | | | |
|---|---|---|---|
| EP | 0726937 | | 9/1994 |
| EP | 0677576 | | 3/1995 |
| EP | 0700987 | | 3/1996 |
| EP | 747042 | | 12/1996 |
| EP | 0827529 | | 3/1998 |
| EP | 0872543 | | 10/1998 |
| EP | 0876465 | | 11/1998 |
| EP | 0882121 | | 12/1998 |
| EP | 1238645 | | 9/2002 |
| EP | 1238654 | | 9/2002 |
| GB | 2285052 | | 2/1994 |
| JP | 3212500 | | 9/1991 |
| JP | 2000230194 | | 8/2000 |
| JP | 2001158981 | | 6/2001 |
| NO | 2007002895 | | 11/2004 |
| WO | WO9112354 | | 8/1991 |
| WO | WO9407974 | | 4/1994 |
| WO | WO9407984 | | 4/1994 |
| WO | WO9407985 | | 4/1994 |
| WO | WO9407986 | | 4/1994 |
| WO | WO 95/22540 | * 8/1995 ........... C07D 403/06 |
| WO | WO9603149 | | 2/1996 |
| WO | WO9716520 | | 5/1997 |
| WO | WO9725405 | | 7/1997 |
| WO | WO9920271 | | 4/1999 |
| WO | WO0113956 | | 3/2001 |
| WO | WO0134745 | | 5/2001 |
| WO | WO02052066 | | 7/2002 |
| WO | WO02069960 | | 9/2002 |
| WO | WO02078648 | | 10/2002 |
| WO | WO03007901 | | 1/2003 |
| WO | WO03092617 | | 11/2003 |
| WO | WO2004035015 | | 4/2004 |
| WO | WO2004037197 | | 5/2004 |
| WO | WO2004082628 | | 9/2004 |
| WO | WO2004089396 | | 10/2004 |
| WO | WO2006097191 | | 9/2006 |
| WO | WO2006097192 | | 9/2006 |
| WO | WO2006097193 | | 9/2006 |
| WO | WO2007113830 | | 10/2007 |
| WO | WO2008003677 | | 1/2008 |
| WO | WO2008046795 | | 4/2008 |
| WO | WO2008156798 | | 12/2008 |
| WO | WO2009062746 | | 5/2009 |
| WO | WO2009087242 | | 7/2009 |
| WO | WO2010026010 | | 3/2010 |
| WO | WO2010065567 | | 6/2010 |
| WO | WO2010121232 | | 10/2010 |
| WO | WO2010132440 | | 11/2010 |
| WO | WO2011031503 | | 3/2011 |
| WO | WO2011075654 | | 6/2011 |
| WO | WO2011150221 | | 12/2011 |

OTHER PUBLICATIONS

Pastor, I.M. et al. "Bioactive N-Phenylimidazole Derivatives" Current Chemical Biology, 2009, 3, 385-408.

Feghali, C.A. et al. "Cytokines in Acute and Chronic Inflammation" Frontiers in Bioscience 2, 12-26, Jan. 1, 1997.

Franklin, M.R. "Comparative 1-Substituted Imidazole Inhibition of Cytochrome P450 Isozyme-Selective Activities in Human and Mouse Hepatic Microsomes" Drug Metabolism Reviews 39: 309-322, 2007.

Thatcher, J.E. et al., "The Role of CYP26 Enzymes in Retinoic Acid Clearance" Expert Opin. Drug Metab. Toxicol. (2009) 5(8):875-886.

Ahmad, N. et al. "Cytochrome P450: a target for drug development for skin diseases" *J.Invest. Dermatol.*, 123: 417-425, 2004.

Fisher, G.J. et al. "Molecular Mechanisms of Retinoid Actions in Skin" *FASEB J.* Jul. 1996;10(9):1002-13.

Rocquet, C. et al. "A Natural Way to Relieve the Skin from Erythema: Grevilline" Cosmetic Science Technology 2008, 1 page.

Duell, E.A. et al. "Human Skin Levels of Retinoic Acid and Cytochrome P-450-derived 4 Hydroxyretinoic Acid after Topical Application of Retinoic Acid iIn Vivo Compared to Concentrations Required to Stimulate Retinoic Acid Receptor—Medicated Transcription In Vitro" J. Clin. Invest. Oct. 1992; 90(4): 1269-1274.

Haranda, A. et al. "Essential Involvement of Interleukin-8 (IL-8) in Acute Inflammation" Journal of Leukocyte Biology, vol. 56, Nov. 1994; 6 pages.

Kang, S. et al. "Liarozole Inhibits Human Epidermal Retinoic Acid 4-Hydroxylase Activity and Differentially Augments Human Skin Response to Retinoic Acid and Retinol In Vivo" The Journal of Investigative Dermatology; vol. 107, No. 2 Aug. 1996; 6 pages.

Kollman, J.M. "The Structure of the y-Tubulin Small Complex: Implications of its Architecture and Flexibility for Microtubule Nucleation" Molecular Biology of the Cell, vol. 19, 207-215, Jan. 2008.

Kafi, R. et al. "Improvement of Naturally Aged Skin With Vitamin A (Retinol)" Arch Dermatol. 2007; 143: 606-612.

McSorley, L.C. et al. "Identification of Human Cytochrome P450 Isoforms That Contribute to All-Trans Retinoic Acid 4-Hydroxylation" *Biochemical Pharmacology*, 60: 517-526, 2000.

Lucker, G.P., et al. Oral treatment of ichthyosis by the cytochrome P-450 inhibitor liarozole. Br. J. Dermatol., 136(1): 71-75, 1997.

Nadin, L. et al. "All-trans-retinoic Acid 4-Hydroxylation in Human Liver Microsomes: in vitro Modulation by Therapeutic Retinoids" Br J Clin Pharmacol 1996; 41: 609-612.

Cali, J. et al. "Promega's P450-G10 Luminescent Cytochrome P450 Assay Using the FLUOstar OPTIMA" Application Note 151, Rev. Apr. 2007; 2 pages.

Ahmad, M. "Study on Cytochrome P-450 Dependent Retinoic Acid Metabolism and its Inhibitors as Potential Agents for Cancer Therapy" Sci. Pharm. 2011; 79: 921-935.

Antoniou, C. et al. "Photoaging: Prevention and Topical Treatments" Am J Clin Dermatol 2010; 11 (2): 95-102.

Kang, S. et al. "Photoaging Therapy with Topical Tretinoin: An Evidence-Based Analysis" Journal of the American Academy of Dermatology Aug. 1998; 7 pages.

Ricketts, J.R. et al. "Nutrition and Psoriasis" Clinics in Dermatology (2010) 28, 615-626.

Yengi, L.G. et al. "Quantitation of cytochrome P450 mRNA levels in human skin" Anal. Biochem., 316: 103-110, 2003.

Itokawa, D. et al. "Quantitative Structure—Activity Relationship for Inhibition of CYP2B6 and CYP3A4 by Azole Compounds—Comparison with Their Binding Affinity" QSAR Comb. Sci. 28, 2009, No. 6-7, 629-636.

Verfaille, C.J. et al. "Retinoic Acid Metabolism Blocking Agents (RAMBAs): A New Paradigm in the Treatment of Hyperkeratotic Disorders" JDDG; 2008 • 6:355-364.

(56) References Cited

OTHER PUBLICATIONS

Njar, V.C.O., et al. "Retinoic acid metabolism and blocking agents (RAMBAs) for treatment of cancer and dermatological diseases" *Bioorganic& Medicinal Chemistry*, 14: 4323-4340, 2006.

Mukherjee, S. et al. "Retinoids in the Treatment of Skin Aging: An Overview of Clinical Efficacy and Safety" Clinical Interventions in Aging 2006:1(4) 327-348.

Kang, S et al. "The retinoid X receptor agonist 9-cis retinoic acid and the 24-hydroxylase inhibitor ketoconazole increase the activity of 1,25-dihydroxyvitamin D3 in human skin in vivo" *J. Invest. Dermatol.*, 108(4): 513-518, 1997.

Lucker, G.P.H. et al. "Topical liarozole in ichthyosis:a double-blind, left-right comparative study followed by a long-term open maintenance study" *Br. J. Dermatol.*, 565-595, 2005.

Mills, K.J. Pharmacological pleiotropy and its potential importance in understanding anti-dandruff activity (part I). SLR, Jun. 2006.

Van Wauwe, J., et al.. "Liarozole, an inhibitor of retinoic acid metabolism, exerts retinoid-mimetic effects in vivo" *J. Pharmacol. Exp. Ther.*, 261(2): 773-779, 1992.

Miller, W.H., Jr. The emerging role of retinoids and retinoic acid metabolism blocking agents in the treatment of cancer. *Cancer*, 83(8): 1471-1482, 1998.

Dockx, P., et al. "Inhibition of the metabolism of endogenous retinoic acid as treatment for severe psoriasis: an open study with oral liarozole" *Br. J. Dermatol.*, 133(3): 426-432, 1995.

International Search Report PCT/US2014/015206; Mailing Date Jul. 14, 2014; 16 pages.

Griffiths, C. E.M. et al. "Drug Treatment of Photoaged Skin" Drugs & Aging Apr. 14, 1999 (4): 289-301.

Gelain, F. et al. "Electrospun Microfiber Tubes and Self-Assembling Peptides Stimulate Neural Regeneration in Rat Sciatic Nerve Transections" NSTI-Nantech 2007, www.nsti.org, vol. 2, 2007; 4 pages.

P450-G10 Assays, Technical Bulletin No. 325; Promega Corporation Jun. 2003; 54 pages; www.promega.com (Revised Jul. 2014).

Stratigos, A.J. "The Role of Topical Retinoids in the Treatment of Photoaging" Drugs 2005; 65 (8): 1061-1072.

\* cited by examiner

COSMETIC COMPOSITIONS CONTAINING SUBSTITUTED AZOLE AND METHODS FOR ALLEVIATING THE SIGNS OF PHOTOAGED SKIN

FIELD OF THE INVENTION

Cosmetic compositions and methods for alleviating the signs of photoaged skin using substituted azole compounds. In select compositions, the substituted azole is 1-phenylimidazole, 4-phenylimidazole, or combinations thereof.

BACKGROUND OF THE INVENTION

Skin aging is a multifactorial process driven by both intrinsic (chronological aging) and extrinsic (environmental) factors. The primary environmental factor that damages human skin to cause premature aging is UV irradiation from the sun. Sun-induced skin aging ("photoaging"), like chronological aging, is a cumulative process. However, unlike chronological aging, which depends solely on the passage of time, photoaging is a function of the degree to which one is exposed to the sun over a lifetime. The photoaging process is cumulative, with UV irradiation invoking a complex sequence of molecular responses that progressively damage the skin.

Signs of photoaged skin include wrinkles, pigmented lesions such as freckles, lentigines, and patchy hyperpigmentation. Other signs include a loss of tone and elasticity, increased skin fragility, areas of purpura, keratoses, and telangiectasis. Epidermal atrophy and discrete changes in collagen and elastic fibers characteristically occur. In severely photoaged skin, the collagen fibers are fragmented and thickened. Elastic fibers also appear fragmented and may exhibit progressive cross-linkage and calcification. These alterations in collagen and elastic fibers have been demonstrated to worsen with continued exposure.

The most effective measure to prevent photoaging is total avoidance of UV irradiation. Since total avoidance of sunlight is an impractical solution, blocking UV irradiation with protective clothing and/or sunscreen is a common, although not entirely satisfying, alternative. Such protective measures can help prevent future UV damage, but they do nothing to remedy past damage.

Various topical agents have also been used in an effort to treat photoaged skin. Clinically proven to not only reverse but also to prevent the signs of photoaging, retinoids are a class of materials widely recognized as effective. Retinoids are natural and synthetic compounds derived from all-trans-retinol, commonly known as Vitamin A. Retinol is transported to various cells where it is stored as a Vitamin A esters or oxidized sequentially through a retinaldehyde intermediate to all-trans-retinoic acid. Retinoids are important for embryonic development, the survival of lymphocytes, normal vision, and epithelial tissue differentiation. As such, they are critical for normal tissue function and human survival.

Although they can be very effective, retinoids are not well tolerated by many people. Common side effects associated with topically applied retinoids include burning and stinging of the skin, peeling, redness, and heightened photosensitivity. Furthermore, the therapeutic effect decreases over time, necessitating the use of increasingly higher retinoid levels to maintain the same level of benefit. Retinoid side effects are largely dose-dependent. As a result, many individuals with a sensitivity to retinoids cannot tolerate levels sufficient to provide the desired positive results. Additionally, retinoids are rapidly metabolized by the body, resulting in the need for higher doses than would otherwise be required to achieve the desired therapeutic effects.

Accordingly, there still remains a need for alternative compositions and methods that can prevent and/or reverse the signs of photoaging.

SUMMARY OF THE INVENTION

The present invention provides a method of alleviating the signs of photoaged skin comprising: (a) identifying a UV-exposed skin surface; and (b) applying to the skin surface a composition comprising an effective amount of a substituted azole compound represented by the structure:

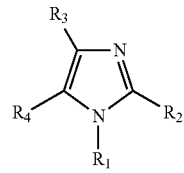

where:
R1: is an alkyl or phenyl electron donating group
R2: is hydrogen
R3 and R4 (which may be identical or different): do not form a fused ring, and each is independently selected from the monodentate group consisting of H, alkyl, and phenyl.

The substituted azole compound can be one or a combination of more than one substituted azole compound. In some embodiments, the substituted azole compound is 1-phenylimidazole:

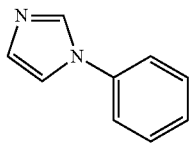 [SMILES: c1ccc(-n2ccnc2)cc1]

In other embodiments, the substituted azole compound is 4-phenylimidazole:

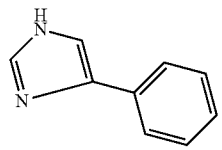 [SMILES: c1ccc(-c2c[nH]cn2)cc1]

In some compositions, the substituted azole compound is a combination of 1-phenylimidazole and 4-phenylimidazole.

The composition comprises an effective amount of the substituted azole compound. In some embodiments, the composition comprises up to 20%, 10%, 5%, 3%, or 1%, and alternatively at least 0.001%, 0.01%, 0.1%. 0.2%, or 0.5%, by weight of the total composition, of the substituted azole compound. Suitable ranges can include any combination of the lower and upper limits, for example from 0.001% to 20%; from 0.001% to 1%; or from 0.5% to 10%, by weight of the composition, of the substituted azole compound. The amounts listed herein are only to be used as a guide, as the optimum amount will depend on the specific substituted azole compound selected, since their potency does vary considerably.

The composition also comprises a dermatologically acceptable carrier. The composition can also include optional ingredients as desired, such as a sunscreen active, an anti-inflammatory agent, and/or a skin tone agent. Exemplary skin tone agents can include vitamin B3 compounds, sugar amines, hexamidine compounds, salicylic acid, and/or 1,3-dihydroxy-4-alkylbenzene.

Alternatively, optional ingredients can be delivered in a second composition that is applied contemporaneously as part of a regimen. In such embodiments, a first composition comprises the substituted azole compound and a second composition comprises desired optional ingredients.

The composition is applied for a period of time sufficient to alleviate one or more signs of photoaging. Such application can occur before, during, and/or after UV exposure. In particular embodiments, the composition is applied to a facial skin surface, which may include the forehead, perioral, chin, periorbital, nose, and/or cheek.

The present invention may take other forms. Further forms of the present invention will be appreciated in the detailed description that follows.

DETAILED DESCRIPTION OF THE INVENTION

The present invention provides a method of alleviating the signs of photoaged skin. As used herein, "alleviating the signs of photoaged skin" is broad enough to include not only minimizing and/or preventing and/or delaying at least one sign of photoaging, but also treating photoaged skin to effect visually and/or tactilely perceptible positive change (i.e., benefit) in appearance and/or feel of at least one sign of photoaging.

"Signs of photoaged skin" include, but are not limited to, all outwardly visible and/or tactilely perceptible manifestations of skin photoaging. Such signs can include wrinkles and coarse deep lines, fine lines, crevices, bumps, and large pores; thinning of keratinous tissue (e.g., the epidermis and/or dermis and/or sub-dermal layers of the skin); decreasing the convolution of the dermal-epidermal border (also known as the rete ridges); hyperpigmentation (e.g., age spots); loss of skin elasticity (e.g., due to loss, damage and/or inactivation of functional skin elastin, resulting in such conditions as elastosis, sagging, and/or loss of skin recoil from deformation); and/or skin discoloration (e.g., blotchiness, sallowness).

The method of the present invention comprises: (a) identifying a UV-exposed skin surface; and (b) applying to the skin surface a composition comprising an effective amount of a substituted azole compound for a period of time sufficient to alleviate one or more signs of photoaging. Unless otherwise indicated expressly or by context, the term "substituted azole" refers to one or more substituted azole compounds represented by the structure set forth herein. "UV-exposed skin surface" means a skin surface that has been or will be exposed to UV-radiation (e.g., sunlight). "Applying" means to apply or spread the composition onto a human skin surface (i.e., epidermis).

An "effective amount" of a substituted azole compound or of a composition containing such substituted azole compound means an amount of such compound or composition sufficient to significantly (i.e., statistically significant) alleviate one or more signs of photoaging. The particular amount that is effective depends on the specific substituted azole compound selected, since the potency of these compounds does vary.

In some embodiments, the composition comprises up to 20%, 10%, 5%, 3%, or 1%, and alternatively at least 0.001%, 0.01%, 0.1%. 0.2%, or 0.5%, by weight of the total composition, of the substituted azole compound. Suitable ranges can include any combination of the lower and upper limits, for example from 0.001% to 20%; from 0.001% to 1%; or from 0.5% to 10%, by weight of the composition, of the substituted azole compound. These exemplary amounts are only to be used as a guide, as the optimum amount will depend on the potency of the specific substituted azole compound. Hence, the amount of some compounds useful in the present invention may be outside the ranges set forth herein. Determining the effective amount for the chosen substituted azole compound is within the knowledge of one skilled in the art.

The composition further comprises a dermatologically acceptable carrier. The term "dermatologically acceptable" as used herein means that the compositions or components described are suitable for use in contact with human skin tissue without undue toxicity, incompatibility, instability, allergic response, and the like.

The substituted azole compound of the present invention is represented by the structure:

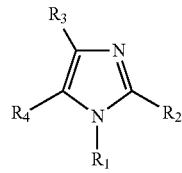

where: R1 is an alkyl or phenyl electron donating group; R2 is hydrogen; R3 and R4 (which may be identical or different) do not form a fused ring and each is independently selected from the monodentate group consisting of H, alkyl, and phenyl. The N-substituted azole compound can be one or a combination of more than one substituted azole compound.

In some embodiments, the substituted azole compound is 1-phenylimidazole:

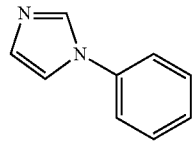

In other embodiments, the substituted azole compound is 4-phenylimidazole:

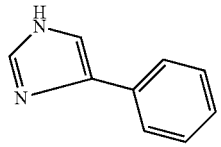 [SMILES: c1ccc(-c2c[nH]cn2)cc1]

In some compositions, the substituted azole compound is a combination of 1-phenylimidazole and 4-phenylimidazole.

I. Compositions

The present invention relates to various compositions and, more specifically, to compositions for application to a skin surface. The compositions may be in a wide variety of product forms that include, but are not limited to, solutions, suspensions, lotions, creams, gels, toners, sticks, pencil, sprays, aerosols, ointments, cleansing liquid washes and solid bars, shampoos and hair conditioners, pastes, foams, powders, mousses, shaving creams, wipes, strips, patches, electrically-powered patches, wound dressing and adhesive bandages, hydrogels, film-forming products, facial and skin masks (with and without insoluble sheet), make-up such as foundations, eye liners, and eye shadows, and the like. The composition form may follow from the particular dermatologically acceptable carrier chosen, if present in the composition.

A. Substituted Azole Compound

Compositions of the present invention comprise an effective amount of a substituted azole compound represented by the structure:

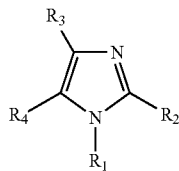

where: R1 is an alkyl or phenyl electron donating group; R2 is hydrogen; R3, and R4 (which may be identical or different) do not form a fused ring and each is independently selected from the monodentate group consisting of H, alkyl, and phenyl.

Electron donating groups have a lone pair of electrons on the atom directly bonded to the ring. The electron donating group increases the aromatic ring's electron density through a resonance donation effect. This is a very stable resonance form, as the resulting carbocation is stabilized by the electron donating group. More stable intermediates (the carbocation) have lower transition state energies and thus a faster reaction rate, resulting in substituents being preferentially directed to positions where they are in conjugation with the aromatic ring. Electron donating groups on an aromatic ring are said to be "activating", because they increase the rate of the second substitution so that it is higher than that of the standard aromatic molecule.

Applicant has surprisingly discovered that this class of substituted azole compounds can alleviate the signs of photoaging when applied topically. Not to be limited by theory, it is believed that the effectiveness of these particular substituted azole compounds is due to their ability to inhibit cytochrome P450 ("CYP") enzyme activity, and thus function as retinoic acid metabolism blocking agents ("RAMBA"s).

1. Mechanism of Action

Researchers have long appreciated that vitamin A is a critical regulator of growth and differentiation of developing and adult mammalian skin. Vitamin A deficiency causes disruption of normal cellular homeostatic mechanisms, resulting in impairment of skin barrier function. All-trans-retinoic acid ("ATRA"), the biologically most active metabolite of vitamin A, plays a major role in cellular differentiation and proliferation of epithelial tissue.

The main source of retinoic acid ("RA") in humans, excluding therapeutic dosing, is through synthesis from dietary precursors such as B-carotene and retinyl palmitate. Vitamin A is stored primarily in liver stellate cells as retinyl esters, which are hydrolyzed in hepatocytes by retinyl ester hydrolases to retinol. Retinol, the precursor of RA, is the main circulating retinoid and is obtained from retinol through a two-step synthesis in which the conversion of retinol to retinal is the rate limiting step. Retinol is oxidized intracellularly by retinol dehydrogenases to retinal, and retinal is then metabolized by NAD/NADP-dependent retinal dehydrogenases to RA.

While RA is synthesized endogenously in the body from dietary precursors, it may also be administered exogenously, such as via topical retinoid application. Research has shown that ATRA has the ability to not only prevent but also to repair photodamage that occurs in skin cells due to UV exposure. UV exposure depletes endogenous ATRA levels. Thus, maintaining elevated levels of ATRA in cells prior to UV exposure is critical in order to block the cascade of negative effects caused by UV exposure. Even during and for several hours after UV exposure, increasing the ATRA levels prevents UV damage. In addition, elevated ATRA levels have been shown to repair preexisting photoaging.

However, as previously mentioned, therapeutic administration of exogenous (e.g., topical) retinoids, especially prior to UV exposure, has challenges due to enhanced photosensitivity and other concerns. Furthermore, the therapeutic effects of ATRA are undermined by its rapid elimination from the body, mediated primarily through rapid in vivo metabolism by CYP enzymes.

An approach to overcoming the drawbacks associated with exogenous retinoid therapy and/or the rapid elimination of ATRA is to amplify endogenous levels of ATRA by inhibiting the CYP-mediated catabolism of RA using agents known as retinoic acid metabolism blocking agents (RAMBAs). RAMBAs prevent the in vivo catabolism of ATRA by inhibiting the CYP-mediated catabolism enzymes responsible for ATRA elimination. Inhibiting the CYP enzymes blocks their metabolism and prolongs RA residence time at the site of action, thus increasing the level of endogenous ATRA within the cells. This results in higher in vivo ATRA concentrations, thus reducing and/or preferably eliminating the need to apply topical exogenous retinoids to achieve the desired effect.

2. In Vitro Cytochrome P450 Inhibition Assay

Cytochrome P450 is a large and diverse group of enzymes that catalyze the oxidation of organic substances. Some members of the CYP family contribute to the elimination of ATRA by catalyzing its 4-hydroxylation in the mammalian liver and skin, including that of humans as well as swine. Applicant evaluated the potential RAMBA activity of several azoles using pig liver microsomes, a rich source of CYP activity, comprising many different CYP 450 isoforms. Therefore, this approach, while a reasonable way to assess CYP inhibitors with broad activities may or may not be the best way to discover RAMBAs with selectivity for the skin, which has a much more narrow complement of CYP expression. As understanding in this area has progressed, a more specific CYP inhibition assay can be used to provide better predictivity of activity in human skin. Nevertheless, this assay may still be used as a general predictor of overall CYP activity.

As shown in Example 2, several compounds were screened through an in vitro CYP assay using pig liver microsomes to determine their effectiveness as CYP inhibitors and correspondingly potential RAMBAs. It is clear from the data in Table 2 that with the exception of the positive control, ketoconazole, none of the tested materials yielded $IC_{50}$ values at concentrations less than 10 μM. This is likely due to the diversity of CYPs in the microsomal sample, which could dilute the inhibitory activity of CYPs most relevant for ATRA metabolism in the skin.

The metabolism of retinoic acid and vitamin D in the skin is incompletely understood, but there is evidence for the involvement of CYP26A1, CYP3A4 and CYP2C8 in catalyzing the 4-hydroxylation of all-trans RA to 4-hydroxy-RA. It is believed, without being limited by theory, that CYP3A4 may be particularly important for ATRA metabolism in the skin. This is because CYP3A4 is expressed in skin, involved in RA metabolism, a CYP with one of the broadest substrate specificities of all of the known CYPs and available as a human recombinant protein in a commercial kit. Thus, a commercially available CYP3A4 assay was used as a surrogate to predict RAMBA potential in the skin. The method is described in more detail below in Example 3, and the results are illustrated in Table 3. As illustrated in Table 3, the $IC_{50}$ values of several compounds indicate strong inhibition of CYP3A4 when the $IC_{50}$ value is ≤10 μM and weak or no inhibition when the $IC_{50}$ value is >10 μM.

Several simple imidazole structures showed a remarkably high level of inhibitory activity relative to the positive control, ketoconazole. Of particular note are the results for 1-, 2-, and 4-phenylimidazole. These materials are positional isomers, differing from one another only in the location of the phenyl group relative to the imidazole ring. The 1- and 4-phenylimidazole had $IC_{50}$ values in the same range as climbazole, a known 4-hydroxylase inhibitor that is marketed as an antifungal active. However, the 2-phenylimidazole analogue lacked any significant inhibitory activity, indicating that positioning of the imidazole ring relative to the phenyl group seems to play an important structural component for CYP enzyme interaction. Thus, 1- and 4-phenylimidazole elicit CYP inhibitory activity, while 2-phenylimidazole does not. Accordingly, 1- and 4-can serve as effective RAMBAs, boosting the endogenous ATRA concentration. These results demonstrate that substituted azole compounds having the particular structure set forth herein function differently from other compounds, even when those compounds are positional isomers. (The chemical structures of the materials tested in Example 2 can be found in Table 3 of Example 3. For brevity, the structures are not duplicated by inclusion in both tables.)

3. In vitro CYP/CYP3A4 Inhibition Assay

The commercially available P450-GLO™ Assay kit (Promega Corporation, Madison Wis.) was used to screen various compounds for potential CYP activity, specifically CYP3A4A inhibition activity. CYP3A4A is thought to be among the primary CYP isoforms responsible for retinoic acid metabolism in the skin.

Three benchmark agents, liarozole, climbazole, and ketoconazole, were assessed for CYP3A4 inhibition to confirm that the inhibition activity (the $IC_{50}$ for CYP inhibition) measured by the assay corresponded to the activity reported by the published literature.

The results set forth in Table 3 show that the substituted azole compounds having the specific structure set forth herein are CYP inhibitors, and thus function as RAMBAs. Of particular note, once again, are the results for the positional isomers 1-, 2-, and 4-phenylimidazole. Consistent with the results from Example 2's CYP in vitro assay, the R1 substituted 1-phenylimidazole and the R3 substituted 4-phenylimidazole showed inhibitory activity in the CYP3A4 assay, but the R2 substituted 2-phenylimidazole analogue did not. This underscores the importance of the substituted azole structure to the CYP enzyme interaction.

As used in Table 3, "hit" or "no hit" mean, respectively, strong inhibition ($IC_{50}$ value<10 μM) or weak/no inhibition ($IC_{50}$ value >10 μM) of CYP3A4.

B. Dermatologically Acceptable Carrier

The compositions of the present invention may also comprise a dermatologically acceptable carrier (which may be referred to as "carrier") for the composition. The phrase "dermatologically acceptable carrier", as used herein, means that the carrier is suitable for topical application to the skin surface, has good aesthetic properties, is compatible with the actives in the composition, and will not cause any unreasonable safety or toxicity concerns. In one embodiment, the carrier is present at a level of from 50% to 99%, or from 60% to 98%, or from 70% to 98%, or, alternatively, from 80% to 95%, by weight of the composition.

The carrier can be in a wide variety of forms. Non-limiting examples include simple solutions (e.g., aqueous, organic solvent, or oil based), emulsions, and solid forms (e.g., gels, sticks, flowable solids, or amorphous materials). In certain embodiments, the dermatologically acceptable carrier is in the form of an emulsion. Emulsion may be generally classified as having a continuous aqueous phase (e.g., oil-in-water and water-in-oil-in-water) or a continuous oil phase (e.g., water-in-oil and oil-in-water-in-oil). The oil phase of the present invention may comprise silicone oils, non-silicone oils such as hydrocarbon oils, esters, ethers, and the like, and mixtures thereof.

The aqueous phase typically comprises water. However, in other embodiments, the aqueous phase may comprise components other than water, including but not limited to water-soluble moisturizing agents, conditioning agents, anti-microbials, humectants and/or other water-soluble skin care actives. In one embodiment, the non-water component of the composition comprises a humectant such as glycerin and/or other polyols. However, it should be recognized that the composition may be substantially (i.e., less than 1% water) or fully anhydrous.

A suitable carrier is selected to yield a desired product form. Furthermore, the solubility or dispersibility of the components (e.g., extracts, sunscreen active, additional components) may dictate the form and character of the carrier. In one embodiment, an oil-in-water or water-in-oil emulsion is preferred.

Emulsions may further comprise an emulsifier. The composition may comprise any suitable percentage of emulsifier to sufficiently emulsify the carrier. Suitable weight ranges include from 0.1% to 10%, or 0.2% to 5% of an emulsifier, based on the weight of the composition. Emulsifiers may be nonionic, anionic or cationic. Suitable emulsifiers are disclosed in, for example, U.S. Pat. No. 3,755,560, U.S. Pat. No. 4,421,769, and McCutcheon's Detergents and Emulsifiers, North American Edition, pages 317-324 (1986). Suitable emulsions may have a wide range of viscosities, depending on the desired product form.

The carrier may further comprise a thickening agent as are well known in the art to provide compositions having a suitable viscosity and rheological character.

C. Skin Tone Agent

In some embodiments, it may be desirable to include a skin tone agent in the composition. The skin tone agents can be included to further improve overall skin tone. When present, the compositions of the present invention can contain up to 50%, 40%, 30%, 20%, 10%, 5%, or 3%, by weight of the composition, of the skin tone agent. When present, the compositions of the present invention can contain at least 0.001%, 0.01%, 0.1%, 0.2%, 0.5%, or 1%, by weight of the composition, of the skin tone agent. Suitable ranges include any combination of the lower and upper limits including suitable ranges from 0.1% to 50%; from 0.2% to 20%; or from 1% to 10%, by weight of the composition, of the skin tone agent. The amounts listed herein are only to be used as a guide, as the optimum amount of the skin tone agent will depend on the specific active selected since their potency does vary considerably.

Suitable skin tone agents include, but are not limited to, sugar amines, vitamin B3 compounds, arbutin, deoxyarbutin, 1,3-dihydroxy-4-alkylbenzene such as hexylresorcinol, sucrose dilaurante, bakuchoil (4-[(1E,3S)-3-ethenyl-3,7-dimethyl-1,6 octadienyl]phenol or monterpene phenol), pyrenoine (available from Biotech Marine, France), *panicum miliaceum* seed extract, arlatone dioic acid, cinnamic acid, ferulic acid, achromaxyl, methyl nicotinamide, oil soluble licorice extract, folic acid, undecylenic acid (i.e., undecenoic acid), zinc undecylenate, thiamine (Vitamin B1) and its hydrochloride, L-tryptophan, *helianthus annuus* (sunflower) and *vitis vinifera* (grape) leaf extract, carnosine (i.e., dragosine), methyl gentisate, 1,2-hexandiol and 1,2-octandiol (i.e., combination sold as Symdiol 68 by Symrise AG, Germany), inositol, decylenoylphenylalanine (e.g., sold under the tradename Sepiwhite by Seppic, France), kojic acid, hexamidine compounds, and salicylic acid.

In certain embodiments, the skin tone agent is selected from vitamin B3 compounds, sugar amines, hexamidine compounds, salicylic acid, and a 1,3-dihydroxy-4-alkylbenzene such as hexylresorcinol. As used herein, "vitamin $B_3$ compound" means a compound having the formula:

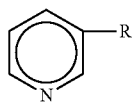

wherein R is —$CONH_2$ (i.e., niacinamide), —COOH (i.e., nicotinic acid) or —$CH_2OH$ (i.e., nicotinyl alcohol); derivatives thereof; and salts of any of the foregoing. As used herein, "sugar amine" includes isomers and tautomers of such and its salts (e.g., HCl salt) and its derivatives. Examples of sugar amines include glucosamine, N-acetyl glucosamine, mannosamine, N-acetyl mannosamine, galactosamine, N-acetyl galactosamine, their isomers (e.g., stereoisomers), and their salts (e.g., HCl salt). As used herein, "hexaminide compound" means a compound having the formula:

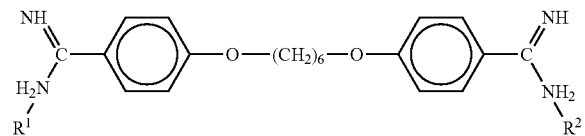

wherein $R^1$ and $R^2$ are optional or are organic acids (e.g., sulfonic acids, etc.). In one embodiment, the hexamidine compound is hexamidine diisethionate.

Furthermore, the skin tone agent of the present invention can include a xanthine compound. As used herein, "xanthine compound" means one or more xanthines, derivatives thereof, and mixtures thereof. Xanthine compounds that can be useful herein include, but are not limited to, caffeine, xanthine, 1-methyl xanthine, theophylline, theobromine, derivatives thereof, and mixtures thereof. In one embodiment, the composition comprises from about 0.1% to about 10% of a xanthine compound, in another embodiment from about 0.5% to about 5% of a xanthine compound, and in yet another embodiment from about 1% to about 2% of a xanthine compound.

D. Anti-Inflammatory Agents

Hyperpigmentation may result from skin inflammation. Transient inflammatory events triggering hyperpigmentation and, more specifically, post-inflammatory hyperpigmentation include, but are not limited to, acne lesions, ingrown hairs, scratches, insect bites, surfactant damage, allergens, and short-term UV exposure. Inflammation induced hyperpigmentation including post-inflammatory hyperpigmentation may be managed by incorporating into the compositions of the present invention an anti-inflammatory agent. When present, the compositions of the present invention can contain up to 20%, 10%, 5%, 3%, or 1% by weight of the composition, of the anti-inflammatory agent. When present, the compositions of the present invention can contain at least 0.001%, 0.01%, 0.1%, 0.2%, 0.3%, 0.5%, or 1%, by weight of the composition, of the anti-inflammatory agent. Suitable ranges include any combination of the lower and upper limits. Exact amounts will vary depending upon the chosen anti-inflammatory agent; determining the appropriate amount is within the knowledge of one of skilled in the art.

Suitable anti-inflammatory agents include, but are not limited to nonsteroidal anti-inflammatory agents ("NSAIDS" including but not limited to ibuprofen, naproxen, flufenamic acid, etofenamate, aspirin, mefenamic acid, meclofenamic acid, piroxicam and felbinac), glycyrrhizic acid (also known as glycyrrhizin, glycyrrhixinic acid, and glycyrrhetinic acid glycoside) and salts such as dipotassium glycyrrhizate, glycyrrhetenic acid, licorice extracts, bisabolol (e.g., alpha bisabolol), manjistha (extracted from plants in the genus *Rubia*, particularly *Rubia cordifolia*), and guggal (extracted from plants in the genus *Commiphora*, particularly *Commiphora mukul*), kola extract, chamomile, and sea whip extract (extracts from plant in the order Gorgonacea), derivatives of any of the foregoing, and mixtures thereof.

E. Sunscreen Actives

The compositions of the subject invention may comprise one or more sunscreen actives (or sunscreen agents) and/or ultraviolet light absorbers. As used herein, "sunscreen active" collectively includes sunscreen actives, sunscreen agents, and/or ultraviolet light absorbers. Sunscreen actives include both sunscreen agents and physical sunblocks. Sunscreen actives may be organic or inorganic. Examples of suitable sunscreen actives are disclosed in Personal Care Product Council's *International Cosmetic Ingredient Dictionary and Handbook*, Thirteenth Edition, as "sunscreen agents."

Suitable sunscreen actives include 2-ethylhexyl-p-methoxycinnamate (commercially available as PARSOL™ MCX), 4,4'-t-butyl methoxydibenzoyl-methane (commercially available as PARSOL™ 1789), 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, menthyl anthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene, zinc oxide, benzylidene camphor and derivatives thereof, titanium dioxide, and mixtures thereof.

When present, the compositions of the present invention can contain up to 20%, 10%, 5%, 3%, or 1% by weight of the composition, of the sunscreen active. When present, the compositions of the present invention can contain at least 0.001%, 0.01%, 0.1%, 0.2%, 0.3%, 0.5%, or 1%, by weight of the composition, of the sunscreen active. Suitable ranges include any combination of the lower and upper limits. Exact amounts will vary depending upon the chosen sunscreen active and the desired Sun Protection Factor (SPF), which is within the knowledge of one of skilled in the art.

F. Other Optional Components

The compositions of the present invention may optionally contain a variety of other ingredients provided that they do not unacceptably alter the benefits of the invention. When present, compositions of the present invention may contain from 0.0001% to 50%; from 0.001% to 20%; or, alternately, from 0.01% to 10%, by weight of the composition, of the optional components. The amounts listed herein are only to be used as a guide, as the optimum amount of the optional components used in a composition will depend on the specific active selected since their potency does vary considerably. Hence, the amount of some optional components useful in the present invention may be outside the ranges listed herein.

The optional components, when incorporated into the composition, should be suitable for use in contact with human skin tissue without undue toxicity, incompatibility, instability, allergic response, and the like. The compositions of the present invention may include optional components such as anti-acne actives, desquamation actives, anti-cellulite agents, chelating agents, flavonoids, tanning active, non-vitamin antioxidants and radical scavengers, hair growth regulators, anti-wrinkle actives, anti-atrophy actives, minerals, phytosterols and/or plant hormones, N-acyl amino acid compounds, antimicrobial or antifungal actives, and other useful skin care actives, which are described in further detail in U.S. application publication No. US2006/0275237A1 and US2004/0175347A1.

The Personal Care Product Council's *International Cosmetic Ingredient Dictionary and Handbook*, Thirteenth Edition, describes a wide variety of non-limiting cosmetic and pharmaceutical ingredients commonly used in the skin care industry, which are suitable optional components for use in the compositions of the present invention. Examples of these ingredient classes include: abrasives, absorbents, aesthetic components such as fragrances, pigments, colorings/colorants, essential oils, anti-caking agents, antifoaming agents, antimicrobials, binders, biological additives, buffering agents, bulking agents, chelating agents, chemical additives, colorants, cosmetic astringents, cosmetic biocides, denaturants, drug astringents, emollients, external analgesics, film formers or materials, opacifying agents, pH adjusters, preservatives, propellants, reducing agents, sequestrants, skin cooling agents, skin protectants, thickeners viscosity modifiers, vitamins, and combinations thereof.

II. Methods of Treatment

Various methods of treatment, application, regulation, or improvement may utilize the aforementioned compositions. Identification of a region of skin subject to photoaging may occur on any skin surface of the body. Skin surfaces of the most concern tend to be those not typically covered by clothing, such as facial skin surfaces, hand and arm skin surfaces, foot and leg skin surfaces, and neck and chest skin surfaces (e.g., décolletage). In particular, identification of the region of photoaged skin may be on a facial skin surface including the forehead, perioral, chin, periorbital, nose, and/or cheek skin surfaces.

One suitable method of improving the appearance of photoaged skin includes the step of topically applying a composition comprising an effective amount of substituted azole to the skin surface, wherein the composition is applied for a period of time sufficient to improve the appearance of the photoaged skin.

The method may comprise the step of applying the composition to the previously identified area of photoaged skin, or an area where one seeks to prevent the appearance of photoaged skin. Many regimens exist for the application of the composition. The composition may be applied at least once a day, twice a day, or on a more frequent daily basis, during a treatment period. When applied twice daily, the first and second applications are separated by at least 1 to 12 hours. Typically, the composition may be applied in the morning and/or in the evening before bed.

The treatment period is ideally of sufficient time to provide an improvement in the appearance of photoaged skin. The treatment period may be at least 1 week, and in some embodiments the treatment period may last 4 weeks or 8 weeks. In certain embodiments, the treatment period will extend over multiple months (i.e., 3-12 months) or multiple years. In one embodiment the composition is applied at least once a day during a treatment period of at least 4 weeks or at least 8 weeks. In one embodiment the composition is applied twice a day during a treatment period of at least 4 weeks or 8 weeks.

The step of applying the composition may be accomplished by localized application. In reference to application of the composition, the terms "localized", "local", or "locally" mean that the composition is delivered to the targeted area (such as age spots) while minimizing delivery to skin surface not requiring treatment. The composition may be applied and lightly massaged into an area of photoaged skin. The form of the composition or the dermatologically acceptable carrier should be selected to facilitate localized application. While certain embodiments of the present invention contemplate applying a composition locally to an area, it will be appreciated that compositions of the present invention can be applied more generally or broadly to one or more skin surfaces.

In some embodiments, the composition may be delivered by a variety of applicators appropriate for localized and general application. Such applicators can include droppers, applicator wands, cotton swabs, or any other suitable device. Other suitable applicators include SH-0127 pen applicator available from Shya Hsin Plastic Works, Inc., Taiwan and either the Xpress Tip or liquid filled swab available from SwabPlus, Inc., China. The applicator may be configured to easily apply the composition to a sign of photoaged skin, for example, age spots having an approximate diameter between about 2 mm and about 10 mm and allowing for a dosed amount of the composition of between about 1 to about 50 $\mu L/cm^2$ or between about 1 to about 5 $\mu L/cm^2$. In another embodiment, the composition is applied to the one or more signs of photoaged skin (e.g., age spots) and more generally to one or more facial skin surfaces contemporaneously (i.e., over a period of less than 30 minutes or, more typically, less than 5 minutes).

While some methods described herein contemplate applying the compositions of the present invention with an applicator, it will be appreciated that applicators are not required and the compositions of the present invention can also be applied directly by using one's finger or in other conventional manners.

In one embodiment, the method comprises the steps of applying a first composition comprising an effective amount of substituted azole to a skin surface and of applying a second composition to the skin surface, before or after the first composition. The first and second compositions may be any compositions described herein; however, the second composition may optionally comprise an effective amount of the substituted azole compound present in the first composition. The second composition may comprise one or more skin tone agents, sunscreen actives, anti-inflammatory agents, or other optional components. The first composition may be generally or locally applied, while the second composition may be generally or locally applied to the skin surface including the photoaged skin to which the first composition is applied. In certain embodiments, the skin surface is a facial skin surface which includes one or more of the forehead, perioral, chin, periorbital, nose, and cheek skin surfaces. In another embodiment, the first and second compositions are applied contemporaneously to at least the cheek, forehead, and chin/perioral skin surfaces. For general application to a skin surface and, particularly a facial skin surface, the dosed amount of the first or second composition may be between about 1 to about 50 µL/cm² per application (i.e., per single application to the skin surfaces).

Suitable methods may comprise any one or more of the abovementioned steps. All of the aforementioned steps are applicable to application, treatment, regulation, and/or improvement of photoaging skin appearance.

EXAMPLES

Example 1

Exemplary Compositions

Table 1 sets forth non-limiting examples of the compositions of the present invention. The examples are given solely for the purpose of illustration and are not to be construed as limitations of the present invention, as many variations thereof are possible without departing from the spirit and scope of the invention, which would be recognized by one of ordinary skill in the art. In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minor materials will vary depending on the physical and chemical characteristics of the particular ingredients selected to make the present invention as described herein.

All examples may be used to alleviate one or more signs of photoaging. The present invention may further relate to a regimen involving the localized treatment for one or more photoaging signs by a first composition (e.g., Examples A or B) and a more broad or general facial skin treatment by a second composition (e.g., Examples C or D), which can be applied before or after the localized treatment to improve a particular sign of photoaging (e.g., across the entire face).

TABLE 1

Exemplary Compositions

| Component/% by wt. | Example A | Example B | Example C | Example D |
|---|---|---|---|---|
| 1-phenylimidazole | 0.50 | 1.5 | 0.00 | 1.00 |
| 4-phenylimidazole | 0.50 | 0.00 | 1.50 | 0.75 |
| N-Acetylglucosamine | 0.00 | 0.00 | 2.00 | 0.00 |
| Hexamidine Diisethionate | 0.00 | 0.00 | 0.09 | 0.09 |
| Sepiwhite ™ (Undecylenoyl-phenylalanine, neutralized) (available from SEPPIC) | 0.00 | 0.00 | 0.50 | 0.50 |
| Sepigel 305 ™ (Polyacrylamide + C13-14 isoparaffin + laureth-7) (available from SEPPIC) | 0.00 | 0.00 | 2.00 | 2.00 |
| Dipotassium Glycyrrhizate | 0.00 | 0.10 | 0.10 | 0.30 |
| Hexamidine Diisethionate | 0.00 | 0.00 | 0.09 | 0.09 |
| Homosalate | 0.00 | 0.00 | 0.00 | 9.00 |
| Avobenzone | 0.00 | 0.00 | 0.00 | 3.00 |
| Octocrylene | 0.00 | 0.00 | 0.00 | 2.60 |
| Oxybenzone | 0.00 | 0.00 | 0.00 | 1.00 |
| Octisalate | 0.00 | 0.00 | 0.00 | 4.50 |
| Butylene Glycol (CAS No. 107-88-0) | 5.50 | 5.50 | 5.50 | 5.50 |
| Niacinamide (CAS No. 98-92-0) | 5.00 | 5.00 | 5.00 | 5.00 |
| Glycerin (CAS No. 56-81-5) | 2.50 | 2.50 | 2.50 | 2.50 |
| DC 1503 Fluid ™ (available from DowCorning) | 2.50 | 2.50 | 2.50 | 2.50 |
| Lubrajel Oil ™ (available from Sederma) | 1.44 | 1.44 | 1.44 | 1.44 |
| Phenonip XB ™ (available from Clariant) | 1.25 | 1.25 | 1.25 | 1.25 |
| D-panthenol (CAS No. 81-13-0) | 1.00 | 1.00 | 1.00 | 1.00 |
| Tospearl 2000 ™ (Polymethylsilsesquioxane) (CAS No. 68554-70-1) (available from GE Silicones/Momentive) | 1.00 | 1.00 | 1.00 | 1.00 |
| DL-Alpha Tocopheryl Acetate (CAS No. 7695-91-2) | 0.50 | 0.50 | 0.50 | 0.50 |
| Prodew 400 ™ (available from Ajinomoto) | 0.50 | 0.50 | 0.50 | 0.50 |
| Pemulen TR-2 ™ (Acrylates/C10-30 Alkyl Acrylate Crosspolymer) (available from Noveon) | 0.25 | 0.25 | 0.25 | 0.25 |

TABLE 1-continued

Exemplary Compositions

| Component/% by wt. | Example A | Example B | Example C | Example D |
|---|---|---|---|---|
| Polysorbate 20 (CAS No. 9005-64-5) | 0.25 | 0.25 | 0.25 | 0.25 |
| Sodium Metabisulfite (CAS No. 7681-57-4) | 0.25 | 0.25 | 0.25 | 0.25 |
| Allantoin (CAS No. 97-59-6) | 0.20 | 0.20 | 0.20 | 0.20 |
| Sodium Hydroxide (CAS No. 1310-73-2) (50% solution by weight in water) | 0.17 | 0.17 | 0.17 | 0.17 |
| Disodium EDTA (CAS No. 139-33-3) | 0.10 | 0.10 | 0.10 | 0.10 |
| Xanthan Gum (CAS No. 11138-66-2) | 0.05 | 0.05 | 0.05 | 0.05 |
| Sodium Hyaluronate (CAS No. 9067-32-7) | 0.01 | 0.01 | 0.01 | 0.01 |
| Water (CAS No. 7732-18-5) | QS | QS | QS | QS |
| TOTAL (% by weight of total composition) | 100.00 | 100.00 | 100.00 | 100.00 |

The compositions of the present invention are generally prepared by conventional methods such as are known in the art of making topical compositions. Such methods typically involve mixing of the ingredients in one or more steps to a relatively uniform state, with or without heating, cooling, application of vacuum, and the like. Typically, emulsions are prepared by first mixing the aqueous phase materials separately from the fatty phase materials and then combining the two phases as appropriate to yield the desired continuous phase. The compositions are preferably prepared such as to optimize stability (e.g., physical stability, chemical stability, photostability) and/or delivery of the active materials. This optimization may include appropriate pH (e.g., less than 7), exclusion of materials that can complex with the active agent and thus negatively impact stability or delivery (e.g., exclusion of contaminating iron), use of approaches to prevent complex formation (e.g., appropriate dispersing agents or dual compartment packaging), use of appropriate photostability approaches (e.g., incorporation of sunscreen/sunblock, use of opaque packaging), etc.

Example 2

In Vitro ATRA 4-Hydroxylase Activity Assay to Determine CYP Inhibition

All procedures were carried out under minimal light in order to prevent degradation of the retinoid samples.

Microsomal preparation: one lobe of fresh pig liver was obtained at the time of slaughter from a food-processing company and immediately placed in ice cold 15 mM KH2PO4/250 mM sucrose (pH 7.4) and kept on ice during transportation. A 10 g sample of liver was minced and homogenized in 30 mls of homogenization buffer (15 mM KH2PO4/250 mM sucrose) using a Tekmar homoginizer by pulsing 3 times 20 second pulses. This procedure was repeated for a total of 8×10 g samples of pig liver. The remaining pig liver was cut into 10-g pieces and wrapped in aluminum foil and stored at −80° C. The homogenates from the 8 samples were pooled and centrifuged at 13,000×g for 20 minutes at 4° C. to remove crude debris and the supernatant was further centrifuged at 100,000×g for 70 minutes at 4° C. The microsomal pellets were resuspended into 50 mls of 150 mM KH2PO4/1 mM DTT (pH 7.4) and 1 mL aliquots were stored at −80° C.

100-150 µg of pig liver microsomal protein in 150 mM KH2PO4 is incubated at 37° C. in the presence of radiolabeled ATRA and 5 mM NADPH for 90 min. The final ATRA concentration is 1 µM, as a combination of [20-Methyl-$^3$H] ATRA and unlabeled ATRA. Initially, radiolabeled ATRA may be used to assist in validating the method. Once retention times of retinoid metabolites are identified, unlabeled ATRA is used for screening. Compounds tested as possible competitive substrates are added to the assay 10 min prior to the addition of ATRA. Ethanol, containing 0.1% butylated hydroxytoluene (BHT) as an antioxidant, is used to stop the reactions. For recovery of ATRA the pH of reactions are adjusted to 3.0 before extraction with 0.1N HCl. Retinoids are extracted from the protein aqueous phase with 4 mL hexane, 1 ml 100 µg/ml BHT in water (pH 3). An additional 4 mlL of hexane (pH 3) is used for a second extraction. The organic extractions are pooled, evaporated to dryness using a speed vac, and resuspended in 62.5 µl acetonitrile containing 1 mg/ml BHT. Samples are analyzed by HPLC.

HPLC separation of retinoids: a suitable HPLC system (e.g., Waters Corp., Milford Mass.) containing a Vydac 201 TP54 column (15 cm×46 mm), multi-wavelength detector (Waters 490) set at 350 nm, and a β-RAM detector (IN/US Systems, Tampa, Fla.) is used to separate retinoids. Mobile phases used for gradient elution of retinoids are those of Duell et al., J. Clin. Invest. 1992 October; 90(4): 1269-1274. Mobile phase A is acetonitrile:0.02 M ammonium acetate:acetic acid (1:1:0.01) and mobile phase B is acetonitrile:0.2M ammonium acetate:acetic acid (19:1:0.008). At the start of the HPLC run, solvent A is run 100% followed by a linear gradient to solvent B at 3 minutes, a shallow gradient to 81% solvent B at 38 minutes, and 100% solvent B at 40 minutes. The flow rate is 0.5 mL/min and the total time for separation is 60 minutes. Effluent from the HPLC column flows directly into a flow-through scintillation spectrometer (β-RAM). Because of the sensitivity limitations of the β-RAM spectrometer, it is not used to quantitate peak areas but rather to confirm ATRA and ATRA 4-hydroxylase activity. Calculated peaks areas (using Millenium software—Waters Corp.) of ATRA and ATRA metabolites are used to quantify relative activity levels. Table 2 shows the compounds screened through the in vitro 4-hydroxylase assay. Ketoconazole was used as a positive control, while climbazole is a known 4-hydroxylase inhibitor marketed as an antifungal active.

TABLE 2

Screening results from in vitro 4-hydroxylase inhibition assay

| Compound | IC$_{50}$ (μM) |
|---|---|
| Ketoconazole | 8.8 |
| Climbazole | 47.5 |
| 1-phenylimidazole | 52.5 |
| 4-phenylimidazole | 58.8 |
| 1-benzylimidazole | 77.5 |
| 4,5-diphenylimidazole | 100.0 |
| 1-benzyl-2-methylimidazole | 307.5 |
| Clotrimazole | >500 |
| 2-phenylimidazole | >500 |

Example 3

In Vitro CYP3A4 Inhibition Assay

A commercially available P450-GLO™ Assay kit (Promega Corporation, Madison Wis.) is used to screen various compounds for CYP3A4A inhibition activity. CYP3A4A is thought to be one of the primary CYP isoforms responsible for retinoic acid metabolism in the skin. Three benchmark agents, liarozole, climbazole, and ketoconazole, were assessed for CYP3A4 inhibition to confirm that the inhibition activity (the IC$_{50}$ for CYP3A4 inhibition) measured by the assay corresponds to the activity reported by the published literature.

The results set forth in Table 3 show that the substituted azole compounds having the specific structure set forth herein are CYP inhibitors, and thus function as RAMBAs.

TABLE 3

Screening results from in vitro CYP/CYP3A4 Inhibition Assay

| Structure | Compound | CAS No. | IC$_{50}$ (uM) |
|---|---|---|---|
| [Structure of liarozole hydrochloride] | Liarizole hydrochloride | 145858-50-0 | Hit <0.1 uM (0.08-0.1 uM) |
| [Structure of climbazole] | Climbazole | 38083-17-9 | Hit 0.1 uM |
| [Structure of ketoconazole] | Ketoconozole | 65277-42-1 | Hit 0.5 uM |
| [Structure of clotrimazole] | Clotrimazole | 23593-75-1 | Hit 0.3 uM |
| [Structure of 1-phenylimidazole] | 1-Phenylimidazole | 7164-98-9 | Hit 1 uM |

TABLE 3-continued

Screening results from in vitro CYP/CYP3A4 Inhibition Assay

| Structure | Compound | CAS No. | IC$_{50}$ (uM) |
|---|---|---|---|
| 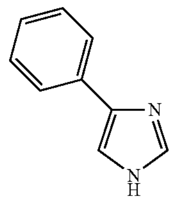 [SMILES: c1ccc(-c2c[nH]cn2)cc1] | 4-Phenylimidazole | 670-95-1 | Hit 1.5 uM |
| 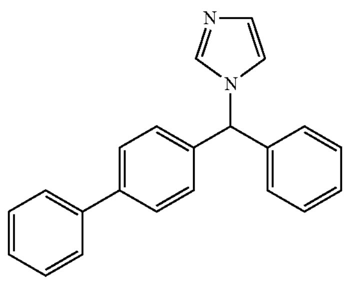 [SMILES: c1ccc(-c2ccc(C(c3ccccc3)n3ccnc3)cc2)cc1] | Bifonazole | 60628-96-8 | Hit 0.8 uM |
| 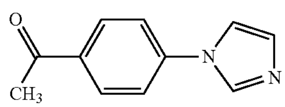 | 4'-(Imidazol-1yl) acetophenome | 10041-06-2 | Hit 0.8 uM |
| 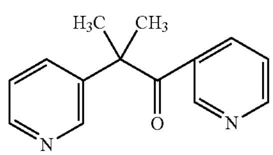 [SMILES: CC(C)(C(=O)c1cccnc1)c1cccnc1] | Metyrapone | 54-36-4 | Hit 3 uM |
| 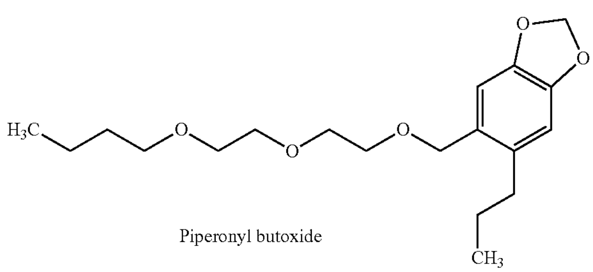 [SMILES: CCCCOCCOCCOCc1cc2c(cc1CCC)OCO2] | Piperonyl butoxide | 51-03-6 | Hit 3 uM |
| 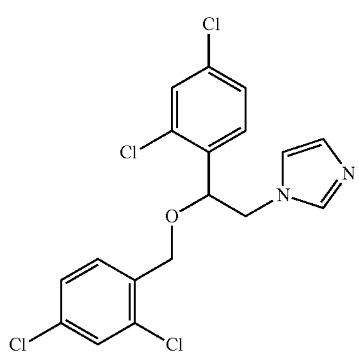 [SMILES: Clc1ccc(COC(Cn2ccnc2)c2ccc(Cl)cc2Cl)c(Cl)c1] | Miconazole | 22916-47-8 | Hit 5 uM |

TABLE 3-continued
Screening results from in vitro CYP/CYP3A4 Inhibition Assay
| Structure | Compound | CAS No. | IC$_{50}$ (uM) |
|---|---|---|---|
| 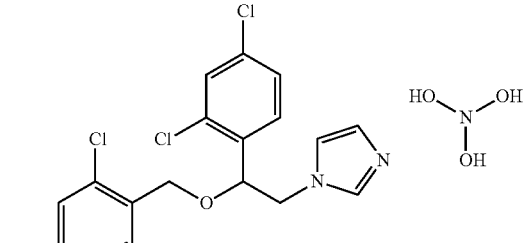 | Miconazole Nitrate | 75319-48-1 | Hit 5 uM |
| 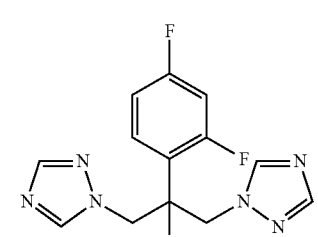 | Fluconazole | 86386-73-4 | Hit ~10 uM |
| 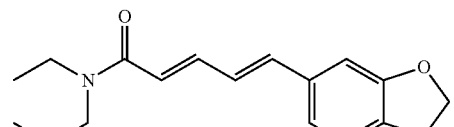 | Piperine | 94-62-2 | Hit ~10 uM |
| 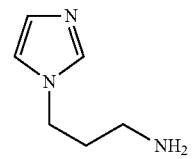 | N-(3-Aminopropyl) imidazole | 5036-48-6 | no hit >10 uM |
| 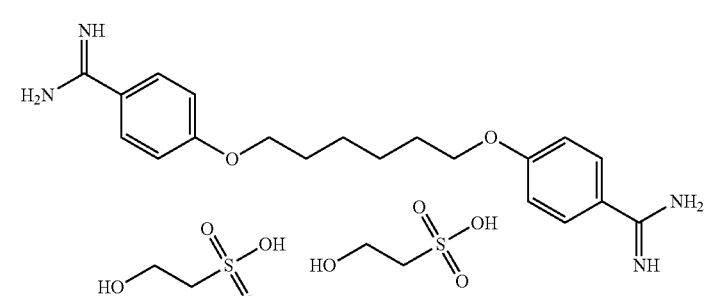 | Hexamidine diisethionate | 659-40-5 | no hit >10 uM |
| 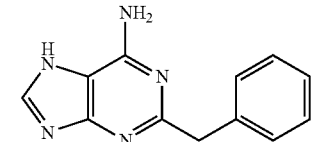 | 3-Benzyladenine | 7280-81-1 | no hit >10 uM |
| 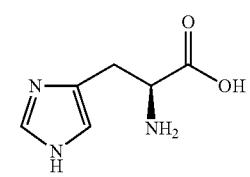 [SMILES: N[C@@H](Cc1c[nH]cn1)C(=O)O] | Histidine | 71-00-1 | no hit >10 uM |

TABLE 3-continued

Screening results from in vitro CYP/CYP3A4 Inhibition Assay

| Structure | Compound | CAS No. | IC$_{50}$ (uM) |
|---|---|---|---|
| 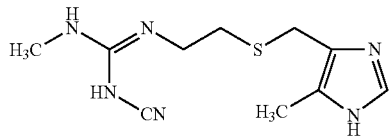 [SMILES: CN/C(=N/CCSCc1nc[nH]c1C)NC#N] | Cimetidine | 51481-61-9 | Near Hit IC50 > 10 uM |
| 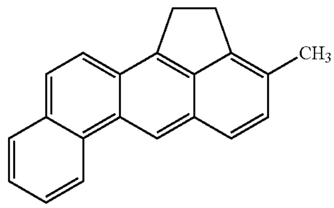 [SMILES: Cc1ccc2cc3c(ccc4ccccc43)c3c2c1CC3] | Methylcholanthrene | 56-49-5 | Near Hit >10 uM |
| 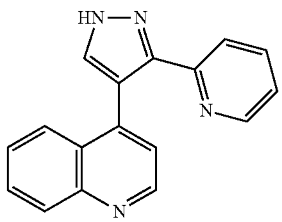 [SMILES: c1ccc(-c2n[nH]cc2-c2ccnc3ccccc23)nc1] | LY-364947 | 396129-53-6 | no hit >10 uM |
| 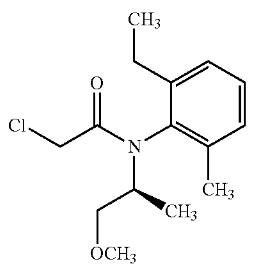 [SMILES: CCc1cccc(C)c1N(C(=O)CCl)[C@@H](C)COC] | Metolachlor | 52118-45-2 | no hit >10 uM |
| 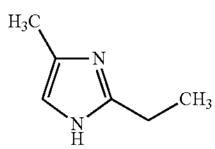 | 2-Ethyl-4-methylimidazole | 931-36-2 | no hit >10 uM |
| 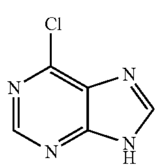 | 6-Chloropurine | 87-42-3 | no hit >10 uM |
| 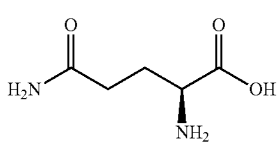 | L-Glutamine | 56-85-9 | no hit >10 uM |
| 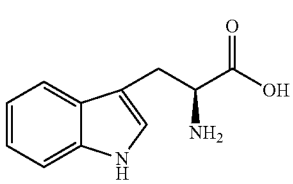 [SMILES: N[C@@H](Cc1c[nH]c2ccccc12)C(=O)O] | L-Tryptophan | 73-22-3 | no hit >10 uM |

TABLE 3-continued

Screening results from in vitro CYP/CYP3A4 Inhibition Assay

| Structure | Compound | CAS No. | IC$_{50}$ (uM) |
|---|---|---|---|
| 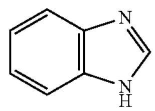 | Benzimidazole | 51-17-2 | no hit >10 uM |
| 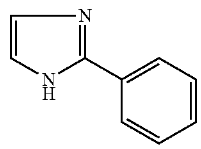 [SMILES: c1ccc(-c2ncc[nH]2)cc1] | 2-Phenylimidazole | 670-96-2 | no hit >10 uM |
| 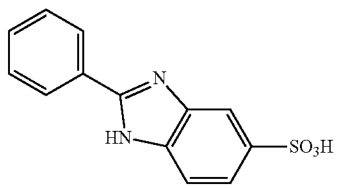 [SMILES: O=S(=O)(O)c1ccc2[nH]c(-c3ccccc3)nc2c1] | 2-Phenyl benzimidazole | 716-79-0 | no hit >10 uM |
| 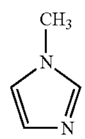 | 1-Methylimidazole | 616-47-7 | no hit >10 uM |
| 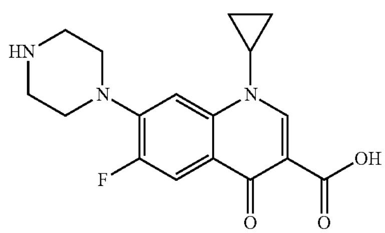 [SMILES: O=C(O)c1cn(C2CC2)c2cc(N3CCNCC3)c(F)cc2c1=O] | Ciprofloxacin HCl | 85721-33-1 | no hit >10 uM |
| 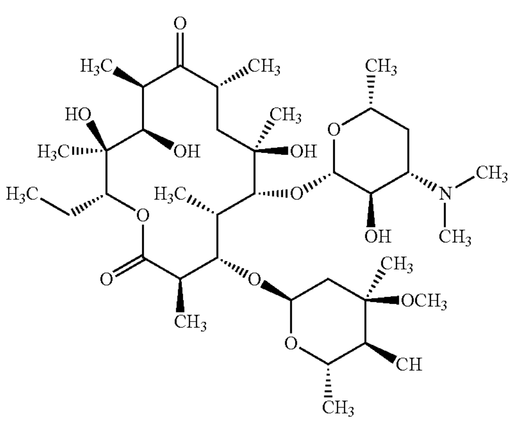 [SMILES: CC[C@H]1OC(=O)[C@H](C)[C@@H](O[C@H]2C[C@@](C)(OC)[C@@H](C)[C@H](C)O2)[C@H](C)[C@@H](O[C@@H]2O[C@H](C)C[C@H](N(C)C)[C@H]2O)[C@](C)(O)C[C@@H](C)C(=O)[C@H](C)[C@@H](O)[C@]1(C)O] | Erythromycin | 114-07-8 | no hit >10 uM |
| 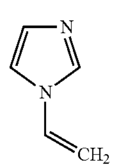 | 1-Vinylimidazole | 1072-63-5 | no hit >10 uM |

TABLE 3-continued

Screening results from in vitro CYP/CYP3A4 Inhibition Assay

| Structure | Compound | CAS No. | IC$_{50}$ (uM) |
| --- | --- | --- | --- |
| 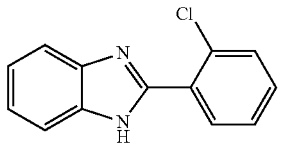 [SMILES: Clc1ccccc1-c1nc2ccccc2[nH]1] | 2-(2-Chlorophenyl) benzimidazole | 3674-96-7 | no hit >10 uM |
| 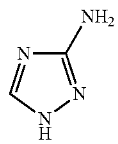 | Amitrol | 61-82-5 | no hit >10 uM |
| 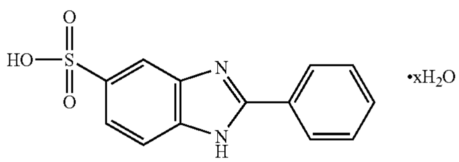 [SMILES: O=S(=O)(O)c1ccc2[nH]c(-c3ccccc3)nc2c1 ; "·xH2O"] | 2-Phenyl-5-benzimidazole sulfonic acid | 27503-81-7 | no hit >10 uM |
| 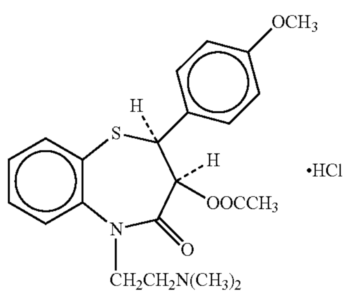 | Diltazem | 42399-41-7 | no hit >10 uM |
| 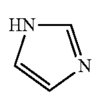 | Imidazole | 288-32-4 | no hit >10 uM |
| 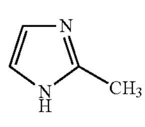 | 2-Methylimidazole | 693-98-1 | no hit >10 uM |
| 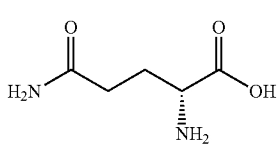 | D-Glutamine | 5959-95-5 | no hit >10 uM |

TABLE 3-continued
Screening results from in vitro CYP/CYP3A4 Inhibition Assay
| Structure | Compound | CAS No. | IC$_{50}$ (uM) |
|---|---|---|---|
| 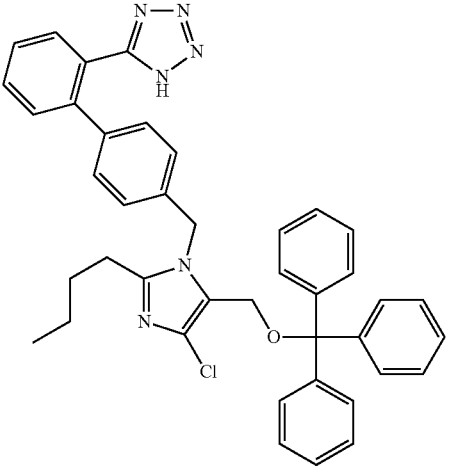 [SMILES: CCCCc1nc(Cl)c(COC(c2ccccc2)(c2ccccc2)c2ccccc2)n1Cc1ccc(-c2ccccc2-c2nnn[nH]2)cc1] | 2-Butyl-4-chloro-5-(hydroxymethyl)imidazole | 79047-41-9 | no hit >10 uM |
| 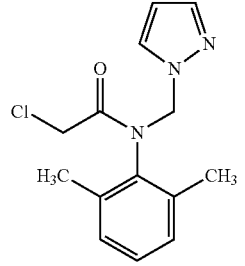 [SMILES: Cc1cccc(C)c1N(Cn1cccn1)C(=O)CCl] | Metazachlor | 67129-08-2 | no hit >10 uM |
| 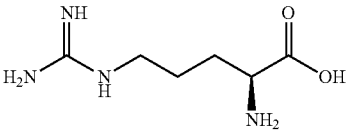 [SMILES: N=C(N)NCCC[C@H](N)C(=O)O] | L-Arginine | 74-79-3 | no hit >10 uM |
| 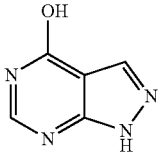 | Allopurinol | 315-30-0 | no hit >10 uM |
| 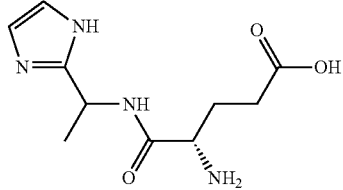 [SMILES: CC(NC(=O)[C@@H](N)CCC(=O)O)c1ncc[nH]1] | Glutamylamidoethyl | 169283-81-2 | no hit >10 uM |
| 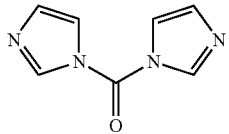 [SMILES: O=C(n1ccnc1)n1ccnc1] | 1'-1-Carbonylimidazole | 530-62-1 | no hit >10 uM |
| 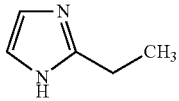 | 2-Ethylimidazole | 1072-62-4 | no hit >10 uM |

TABLE 3-continued

Screening results from in vitro CYP/CYP3A4 Inhibition Assay

| Structure | Compound | CAS No. | IC$_{50}$ (uM) |
|---|---|---|---|
| 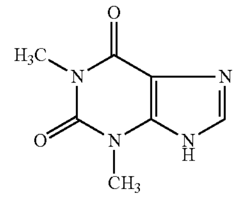 | Theophylline | 58-55-9 | no hit >10 uM |
| 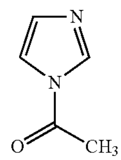 | 1-Acetylimidazole | 2466-76-4 | no hit >10 uM |
| 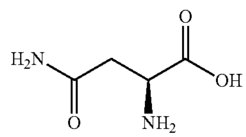 | L-Asparigine | 70-47-3 | no hit >10 uM |
| 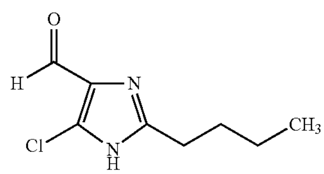 | 2-Butyl-4-chloro-5-formylimidazole | 83857-96-9 | no hit >10 uM |
| 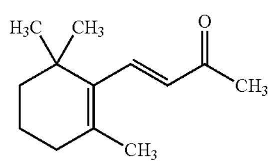 | β-Ionone | 79-77-6 | no hit >10 uM |
| 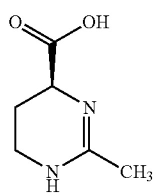 | Ectoine | 96702-03-3 | no hit >10 uM |
| 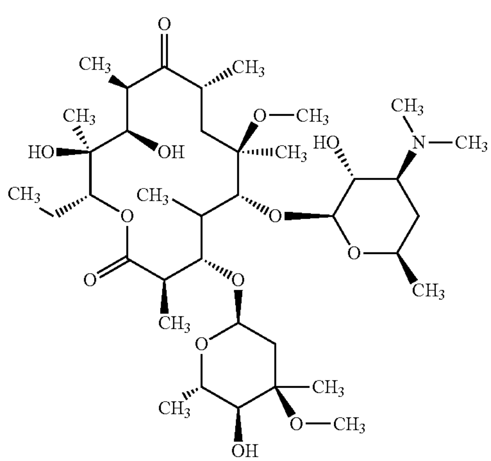 [SMILES: CC[C@H]1OC(=O)[C@H](C)[C@@H](O[C@H]2C[C@@](C)(OC)[C@@H](O)[C@H](C)O2)C(C)[C@@H](O[C@@H]2O[C@H](C)C[C@H](N(C)C)[C@H]2O)[C@](C)(OC)C[C@@H](C)C(=O)[C@H](C)[C@@H](O)[C@]1(C)O] | Clarithromycin | 81103-11-9 | no hit >10 uM |

TABLE 3-continued
Screening results from in vitro CYP/CYP3A4 Inhibition Assay
| Structure | Compound | CAS No. | IC$_{50}$ (uM) |
|---|---|---|---|
| 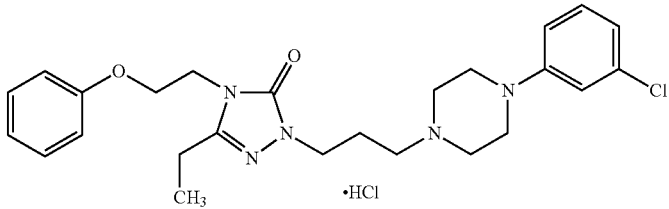 [SMILES: CCc1nn(CCCN2CCN(c3cccc(Cl)c3)CC2)c(=O)n1CCOc1ccccc1 ; Cl] | Nefazodone HCl | 83366-9 | no hit >10 uM |
| 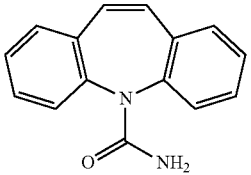 [SMILES: NC(=O)N1c2ccccc2C=Cc2ccccc21] | Carbamazepine | 298-46-4 | no hit >10 uM |
| 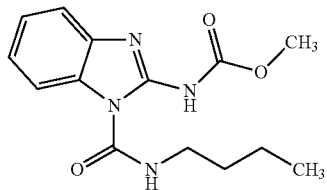 [SMILES: CCCCNC(=O)n1c(NC(=O)OC)nc2ccccc21] | Benomyl | 17804-35-2 | no hit >10 uM |
| 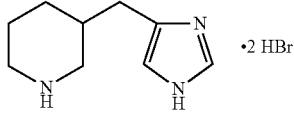 [SMILES: c1nc(CC2CCCNC2)c[nH]1] | Immepip dihydrobromide | 164391-47-3 | no hit >10 uM |
| 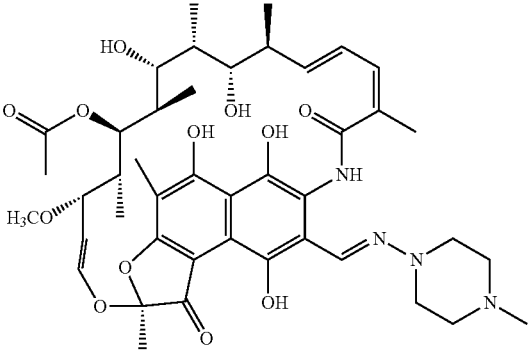 [SMILES: CO[C@H]1/C=C/O[C@@]2(C)Oc3c(C)c(O)c4c(O)c(c(/C=N/N5CCN(C)CC5)c(O)c4c3C2=O)NC(=O)/C(C)=C\C=C\[C@H](C)[C@H](O)[C@@H](C)[C@@H](O)[C@@H](C)[C@H](OC(C)=O)[C@@H]1C] | Rifampicin | 13292-46-1 | no hit >10 uM |
| 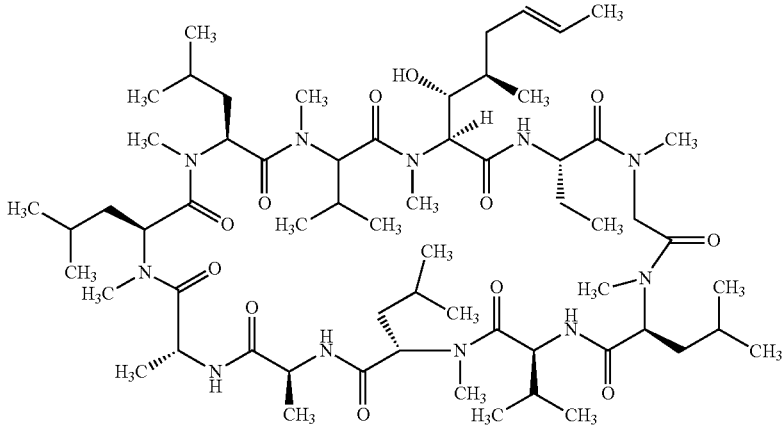 [SMILES: C/C=C/C[C@@H](C)[C@@H](O)[C@H]1C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)C(C(C)C)C(=O)N1C] | Cyclosporin A | 59865-13-3 | no hit >10 uM |

TABLE 3-continued

Screening results from in vitro CYP/CYP3A4 Inhibition Assay

| Structure | Compound | CAS No. | IC$_{50}$ (uM) |
|---|---|---|---|
| 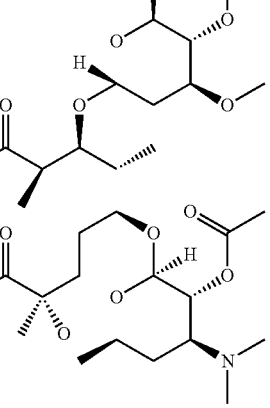 | Troleandomycin | 2751-09-9 | no hit >10 uM |
| 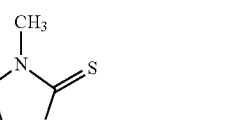 | Methimazole | 60-56-0 | no hit >10 uM |
| 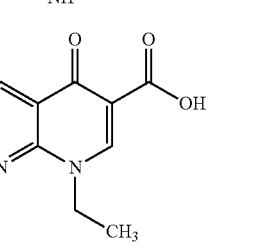 | Nalidixic acid | 389-08-2 | no hit >10 uM |
| 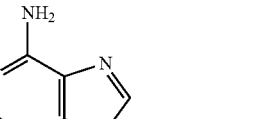 | Adenine | 73-24-5 | no hit >10 uM |
| 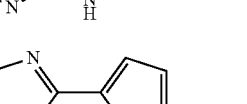 | Fuberidazole | 3878-19-1 | no hit >10 uM |
| 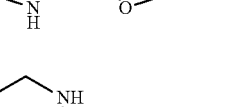 | Kinetin | 525-79-1 | no hit >10 uM |

Example 4

Method of Treatment

A test subject topically applies a composition comprising 0.55% 1-phenylimidazole, by weight in a vehicle, to the entire face one to two times a day for 8 weeks. After treatment, the subject's facial skin feels and appears less aged, and the subject notices an improvement in the appearance of age spots, overall skin tone, and fine lines and wrinkles.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. In particular, U.S. Provisional Application Ser. No. 61/762,551 is incorporated herein by reference in its entirety. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of alleviating the signs of photoaged skin comprising:
   a. identifying a target UV-exposed skin surface in need of treatment;
   b. applying to said target skin surface a composition comprising:
      i. an effective amount of 1-phenylimidazole, 4-phenylimidazole, or a combination thereof; and
      ii. a dermatologically acceptable carrier;
   wherein said composition is applied for a period of time sufficient to alleviate one or more signs of photoaging.

2. The method of claim 1, wherein said composition is applied before, during, or after UV exposure.

3. The method of claim 1, wherein said skin surface is a facial skin surface.

4. The method of claim 1, wherein said facial skin surface is a forehead, perioral, chin, periorbital, nose, or cheek skin surface.

5. The method of claim 1, wherein said composition additionally comprises a sunscreen active.

6. The method of claim 1, wherein said composition additionally comprises an anti-inflammatory agent.

7. The method of claim 1, wherein said composition further comprises a skin tone agent.

8. The method of claim 7, wherein said skin tone agent is selected from the group consisting of vitamin B3 compounds, sugar amines, hexamidine compounds, salicylic acid, 1,3-dihydroxy-4-alkylbenzene, xanthenes, and combinations thereof.

9. The method of claim 1, additionally comprising a step of applying a second composition to the skin surface.

10. The method of claim 1, wherein the second composition comprises a sunscreen active, an anti-inflammatory agent, a skin tone agent, or a combination thereof.

11. The method of claim 10, wherein said skin tone agent is selected from the group consisting of vitamin B3 compounds, sugar amines, hexamidine compounds, salicylic acid, 1,3-dihydroxy-4-alkylbenzene, xanthenes, and combinations thereof.

* * * * *